(12) United States Patent
Schennum (10) Patent No.: US 8,950,395 B2
(45) Date of Patent: Feb. 10, 2015

(54) AEROSOL GENERATOR

(75) Inventor: Steven Michael Schennum, Plainfield, IL (US)

(73) Assignee: Nicoventures Holdings Limited, London (GB)

( * ) Notice: Subject to any disclaimer, the term of this patent is extended or adjusted under 35 U.S.C. 154(b) by 230 days.

(21) Appl. No.: 12/787,257

(22) Filed: May 25, 2010

(65) Prior Publication Data

US 2011/0290244 A1 Dec. 1, 2011

(51) Int. Cl.
*A61M 15/06* (2006.01)
*A61M 11/00* (2006.01)
*A61M 15/00* (2006.01)
*A24F 47/00* (2006.01)
*B65D 83/20* (2006.01)
*B65D 83/30* (2006.01)
*B65D 83/38* (2006.01)
*B65D 83/54* (2006.01)

(52) U.S. Cl.
CPC ............ *A61M 15/009* (2013.01); *A24F 47/002* (2013.01); *A61M 15/06* (2013.01); *B65D 83/20* (2013.01); *B65D 83/30* (2013.01); *B65D 83/384* (2013.01); *B65D 83/54* (2013.01); *A61M 2202/0468* (2013.01)
USPC .................................. 128/202.21; 128/200.23

(58) Field of Classification Search
USPC ............ 128/202.21, 200.14, 200.12, 200.23, 128/201.26, 201.28, 201.21, 202.27, 128/203.14, 203.11, 200.18, 128/200.22–200.24, 203.12, 203.15, 128/203.21; 222/635, 394, 402.14, 402.13, 222/402.12, 402.1; 131/270–273
See application file for complete search history.

(56) References Cited

U.S. PATENT DOCUMENTS

| 3,062,411 A | 11/1962 | De Wayne Miles |
| 3,425,414 A | 2/1969 | La Roche |
| 4,171,000 A | 10/1979 | Uhle |
| 4,223,804 A | 9/1980 | Morris et al. |
| 4,393,884 A | 7/1983 | Jacobs |
| 4,945,929 A | 8/1990 | Egilmex |
| 5,392,768 A | 2/1995 | Johansson et al. |

(Continued)

FOREIGN PATENT DOCUMENTS

| EP | 1170061 A2 | 1/2002 |
| EP | 1 237 610 B1 | 5/2006 |

(Continued)

OTHER PUBLICATIONS

International Search Report and Written Opinion, mailed Aug. 17, 2011, for PCT International Application No. PCT/EP2011/057945, filed May 17, 2011.

(Continued)

*Primary Examiner* — Tan-Uyen (Jackie) T Ho
*Assistant Examiner* — Ned T Heffner
(74) *Attorney, Agent, or Firm* — N W Poulsen; L A Pinol (57) ABSTRACT

An aerosol generator comprising a body, a mouthpiece on the body and a delivery mechanism delivers aerosol for inhalation by a consumer into the mouthpiece by turning the mouthpiece and body relative to one another. The aerosol is generated from liquid dispensed from a canister having a discharge tube depressible inwardly to open an interior valve. A nozzle member is driven inwardly against the discharge tube of the canister when the mouthpiece and body are turned relative to one another, to open the valve and create the aerosol.

12 Claims, 7 Drawing Sheets

(56) References Cited

U.S. PATENT DOCUMENTS

| | | | |
|---|---|---|---|
| 5,404,871 | A | 4/1995 | Goodman et al. |
| 5,549,228 | A | 8/1996 | Brown |
| 5,556,003 | A * | 9/1996 | Johnson et al. ............... 222/39 |
| 5,894,841 | A * | 4/1999 | Voges ..................... 128/203.12 |
| 6,026,990 | A | 2/2000 | Brunswig |
| 6,325,061 | B1 * | 12/2001 | Dagsland ................. 128/203.15 |
| 6,415,784 | B1 | 7/2002 | Christrup et al. |
| 6,494,349 | B1 | 12/2002 | Thompson et al. |
| 7,044,341 | B2 * | 5/2006 | Sanchez ..................... 222/404 |
| 7,069,926 | B2 | 7/2006 | Skellern et al. |
| 2004/0000306 | A1 | 1/2004 | Stradella |
| 2004/0094146 | A1 | 5/2004 | Schiewe et al. |
| 2005/0211733 | A1 | 9/2005 | Healy et al. |
| 2006/0018840 | A1 | 1/2006 | Lechuga-Ballesteros et al. |
| 2006/0278225 | A1 | 12/2006 | MacMichael et al. |
| 2007/0074718 | A1 * | 4/2007 | Austin ..................... 128/200.23 |

FOREIGN PATENT DOCUMENTS

| | | |
|---|---|---|
| GB | 2266466 A1 | 11/1993 |
| WO | WO00/12162 A1 | 3/2000 |
| WO | WO00/53247 A1 | 9/2000 |
| WO | WO02/100469 A2 | 12/2002 |
| WO | WO2005/044354 A1 | 5/2005 |
| WO | WO2009/024578 A2 | 2/2009 |
| WO | WO2009/135729 A1 | 11/2009 |
| WO | WO2011/015825 | 2/2011 |

OTHER PUBLICATIONS

International Preliminary Report on Patentability, mailed May 21, 2012, for PCT International Application No. PCT/EP2011/057945, filed May 17, 2011.

Final Office Action, mailed Aug. 13, 2013, for U.S. Appl. No. 12/787,259.

International Search Report and Written Opinion, mailed Aug. 16, 2011, for PCT International Application No. PCT/EP2011/057603, filed May 11, 2011.

International Preliminary Report on Patentability, mailed Aug. 10, 2012, for PCT International Application No. PCT/EP2011/057603, filed May 11, 2011.

International Search Report and Written Opinion, mailed Aug. 25, 2011, for PCT International Application No. PCT/EP2011/057693, filed May 12, 2011.

International Preliminary Report on Patentability, mailed Nov. 2, 2012, for PCT International Application No. PCT/EP2011/057693, filed May 12, 2011.

International Search Report and Written Opinion, mailed Aug. 4, 2011, for PCT International Application No. PCT/EP2011/057797, filed May 13, 2011.

International Preliminary Report on Patentability, mailed Jul. 6, 2012, for PCT International Application No. PCT/EP2011/057797, filed May 13, 2011.

Invitation to Restrict or Pay Additional Fees, mailed Jul. 6, 2012, for PCT International Application No. PCT/EP2011/057797, filed May 13, 2011.

Non-Final Office Action, dated Dec. 10, 2012, for U.S. Appl. No. 12/787,271.

Non-Final Office Action, dated Jul. 23, 2012, for U.S. Appl. No. 12/787,259.

Non-Final Office Action, dated Jan. 17, 2013, for U.S. Appl. No. 12/787,259.

Non-Final Office Action, dated Jul. 13, 2012, for U.S. Appl. No. 12/787,258.

Final Office Action, dated Jan. 18, 2013, for U.S. Appl. No. 12/787,258.

* cited by examiner

FIG. 11c

AEROSOL GENERATOR

FIELD OF THE INVENTION

This invention relates to a portable aerosol generator which may be hand held and used to deliver aerosol to the mouth of a consumer, for example, but not exclusively an aerosol containing nicotine.

BACKGROUND

A nicotine dispensing aerosol device is disclosed in U.S. Pat. No. 4,945,929, which simulates a smoking article such as a cigarette, without having to burn tobacco.

SUMMARY OF THE INVENTION

This invention provides an aerosol generator comprising a body, a mouthpiece on the body, and a delivery mechanism to deliver aerosol for a consumer into the mouthpiece by turning the mouthpiece and body relative to one another.

The body may include a mounting to receive a canister of pressurised fluid for forming the aerosol, which may include a discharge tube depressible inwardly to open a valve therein to release liquid from the canister through the discharge tube. A nozzle member may be configured to be driven, upon turning the mouthpiece and body relative to one another, to depress the discharge tube of the canister inwardly to open the valve.

The nozzle member can be in threading engagement with the body, and have an end to abut the discharge tube of the canister. The nozzle member can be coupled to the mouthpiece to rotate axially when the mouthpiece is rotated relative to the body and also to slide axially relative to the mouthpiece so as to be driven against the discharge tube of the canister to open the valve and discharge fluid from the canister into the nozzle member.

Radially extending pegs may be provided on the nozzle member that are engaged in a helical groove in the body member to provide the threading engagement of the body and nozzle member.

The coupling of the nozzle member to the mouthpiece may comprise keys on the nozzle member which engage with axial grooves in the mouthpiece to allow rotation of the nozzle member by manual rotation of the mouthpiece and also axial sliding movement.

The nozzle member conveniently includes an orifice to form an aerosol from the fluid discharged from the canister.

BRIEF DESCRIPTION OF THE DRAWINGS

In order that the invention may be more fully understood, embodiments thereof will now be described by way of illustrative example with reference to the accompanying drawings in which:

FIGS. 11A, 11B and 11C are sections of the generator along the planes X-X', Y, Y' and Z-Z' illustrated in FIG. 4a.

DETAILED DESCRIPTION

Figure 1:
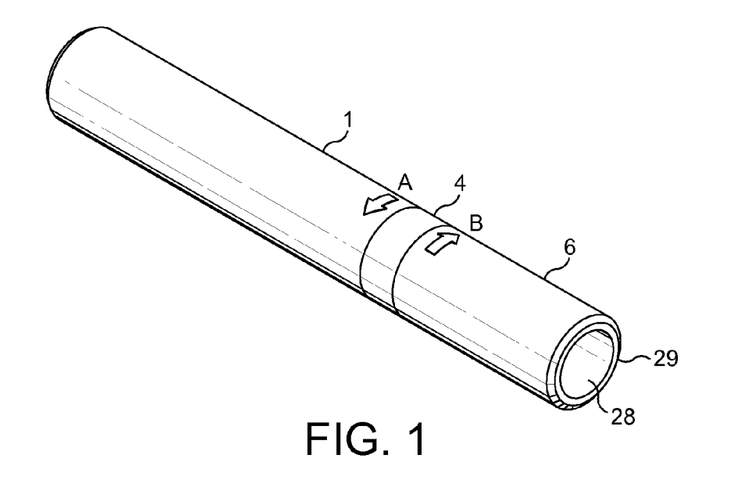
FIG. 1 is a schematic perspective view of an aerosol generator.

FIG. 1 is a perspective view of an aerosol generator. The device is generally cylindrical and designed to be held between the fingers of a consumer's hand to simulate a smoking article such as a cigarette. The generator delivers an aerosol to the mouth of a consumer that may contain nicotine to simulate the smoking of a cigarette.

Arrows A, B indicate the direction to twist in order to actuate the device. The arrows can be embossed or printed on the device for example.

Figure 2:
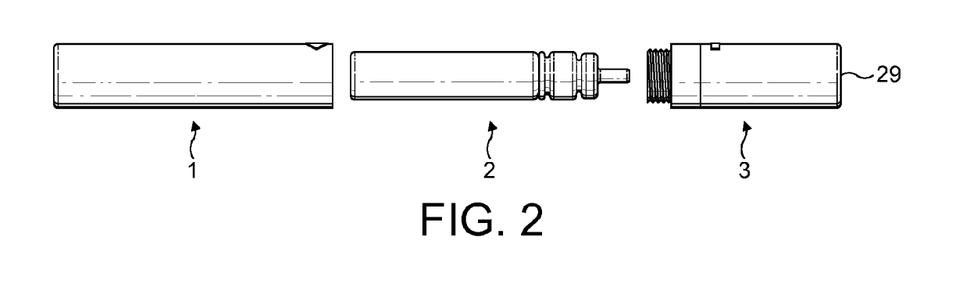
FIG. 2 is a side view of the major components of the generator shown FIG. 1 when disassembled.

FIG. 2 is a side view of the generator during the process of inserting or removing a canister. Canisters can be interchanged in the generator in order to replace empty canisters after use. The major components shown in FIG. 2 include a cylindrical canister housing 1 that is closed at one end, a cylindrical canister 2 that contains the product to be dispensed, and a twist section 3 that contains a mechanism to dispense aerosol from the canister 2. The canister 2 fits into the canister housing 1 and the canister housing is then attached to the twist section 3 using a threaded engagement. Alternative forms of attachment such as snap fitting or bayonet style could also be used. Also the canister housing may be incorporated into the body permanently to provide a device that is discarded after the supply of liquid in the canister is exhausted.

The canister 2 contains a product to be dispensed together with a liquid propellant such as, but not limited to HFA 134a. The specific combination of product and propellant can be altered to yield different flavors and effects. The product may comprise a nicotine-containing liquid with or without additional flavourings and additives, so as to simulate a smoking article such as a cigarette, although it will be appreciated that other compositions may be provided within the canister.

Figure 3:
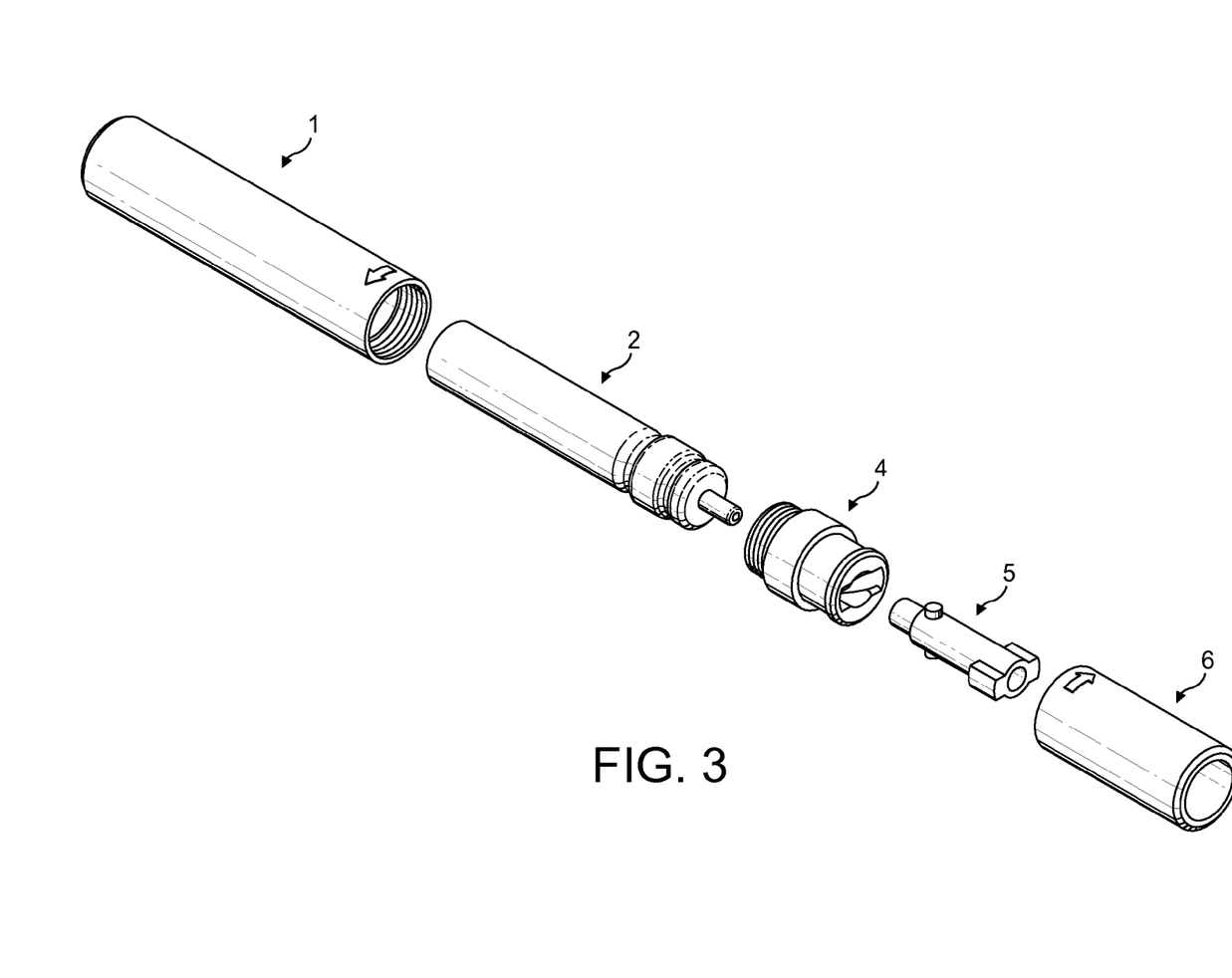
FIG. 3 is an exploded view of the generator.

FIG. 3 is an exploded view of the generator showing the major components: the canister housing 1, canister 2, a body 4, nozzle member 5, and generally cylindrical mouthpiece 6 that is mounted for rotation on the body 4 to supply the aerosol to the mouth of a consumer. The overall look of the device is similar to the look of a filter cigarette where the mouthpiece 6 may correspond in appearance to the filter and the canister housing 1 may correspond visually to the tobacco rod of a conventional cigarette.

Figure 4A:
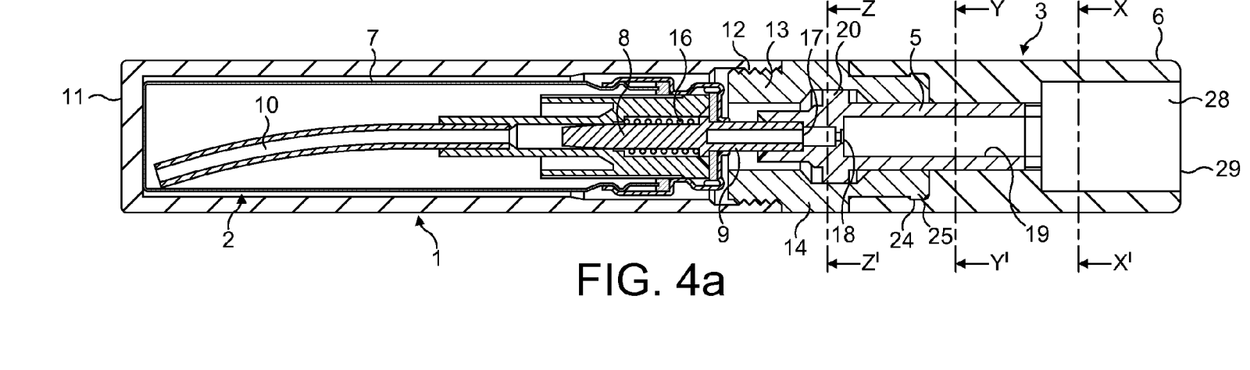
FIGS. 4a and 4b are cross sectional views of the generator with the mouthpiece end twisted outwardly, corresponding to a rest position in which the production of aerosol is inhibited, and with the mouthpiece twisted inwardly to an operative, discharge position to generate the aerosol, respectively.
Figure 4B:
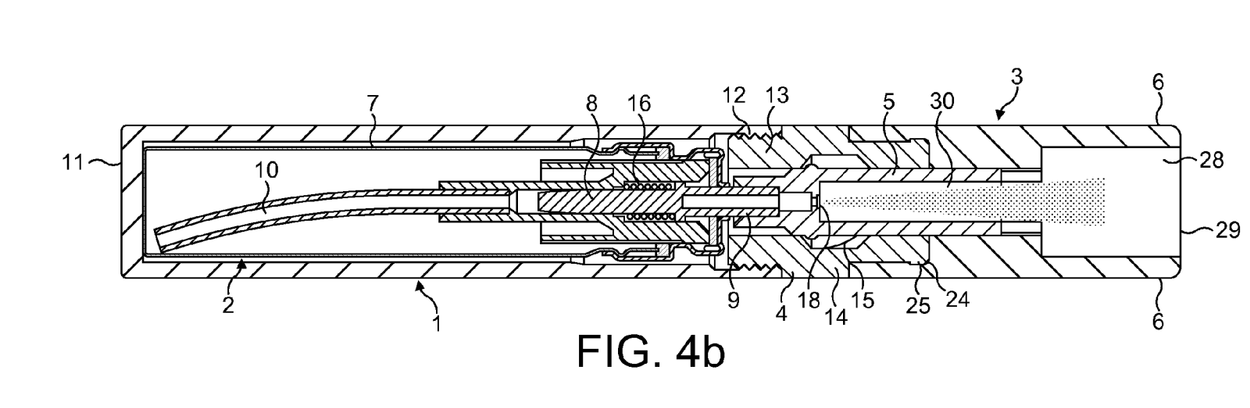

FIG. 4a is a cross section view of the device in an inoperative condition or rest position and FIG. 4b shows the nozzle in a discharge position for spraying aerosol into the mouthpiece 6. The canister 2 has a generally cylindrical body 7 dimensioned to fit within the housing 1 and includes an integral spring loaded valve 8 with a valve stem in the form of a discharge tube 9, which, when driven inwardly against the force of the spring opens the valve to deliver a metered dose of the liquid within the canister through valve inlet tube 10 into the discharge tube 9 to form an aerosol.

The canister housing 1 has a closed, distal end 11 and a threaded proximal end 12 that is threaded onto the distal end of the body member 4. The threaded engagement between the canister housing 1 and the body 4 ensures that valve stem 9 of canister 2 is pressed firmly onto the nozzle member 5.

As shown in FIGS. 4a and 4b, the body member 4 is generally cylindrical with a threaded distal end 13 to engage with the threaded proximal end 12 of the housing 1. The body member 4 includes an axial, tubular passageway that receives the nozzle member 5 and includes a middle section 14 that has an interior thread for driving the nozzle member 5 axially upon rotation of the mouthpiece 6. The interior thread is referenced 15 in FIGS. 5 and 6, which illustrate the body member 4 in more detail.

As shown in FIGS. 4a and 4b, the nozzle member can be driven towards the canister 2 to open the valve 8 by pressing the discharge tube 9 inwardly against the force of an interior valve spring 16, by a twisting action, as will be explained in more detail hereinafter.

Figure 7:
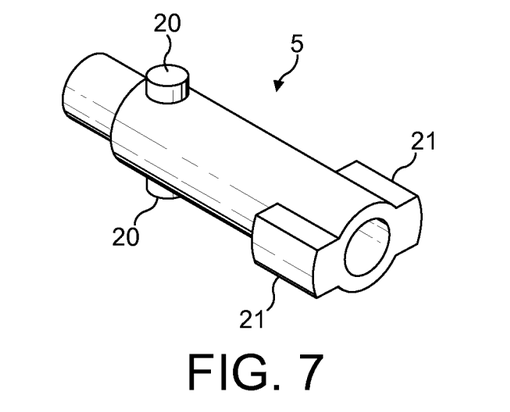
FIG. 7 is a schematic perspective view of the nozzle member shown in FIG. 4.
Figure 8:
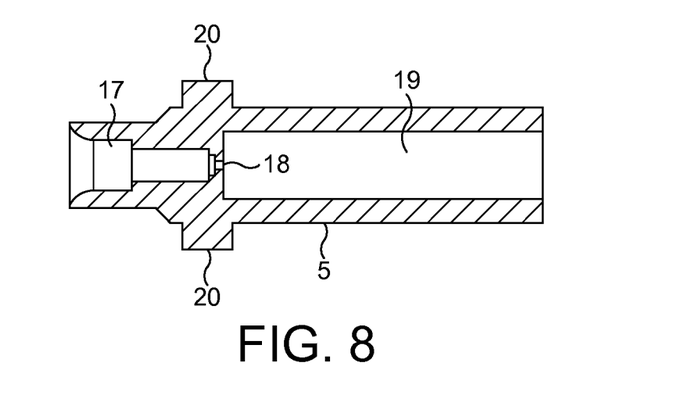
FIG. 8 is a longitudinal section of the nozzle member illustrated in FIG. 7.

Referring to FIGS. 7 and 8, the nozzle member 5 includes a stepped bore 17 which receives the valve stem 9 of the canister 2. An orifice 18 of restricted diameter acts as a nozzle and creates an aerosol from the fluid dispensed from the canister 2. An outlet passageway 19 delivers the aerosol into the mouthpiece 6.

Pegs 20 extending radially outwardly of the nozzle member 5, engage in the thread 15 within the body member 4. Thus, on rotation of the nozzle member 5, it is moved axially in relation to the body member 4.

Figure 9:
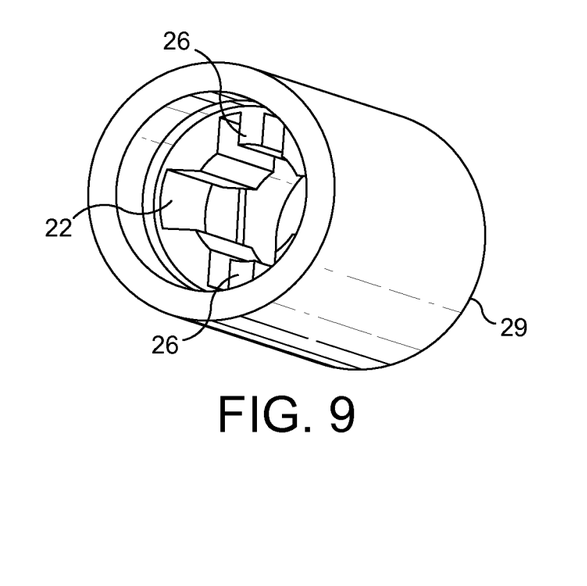
FIG. 9 is a schematic perspective view of the mouthpiece of the device from its distal end.
Figure 10:
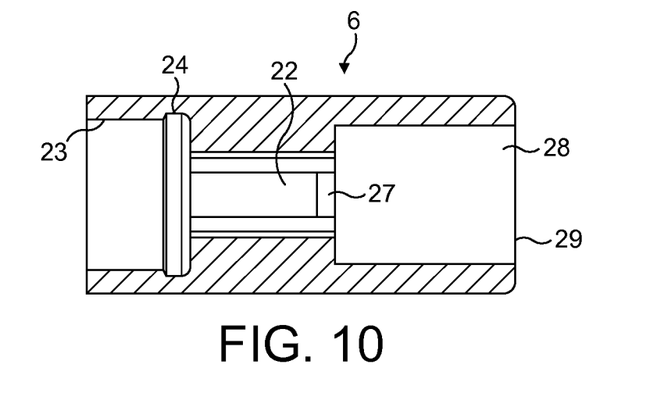
FIG. 10 is a longitudinal sectional view of the mouthpiece illustrated in FIG. 9.
Figure 11A:
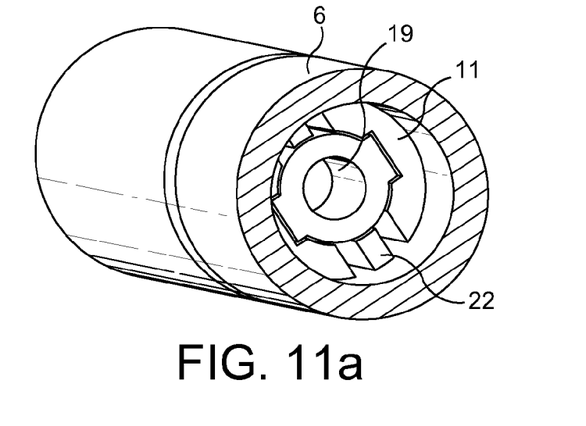
Figure 11B:
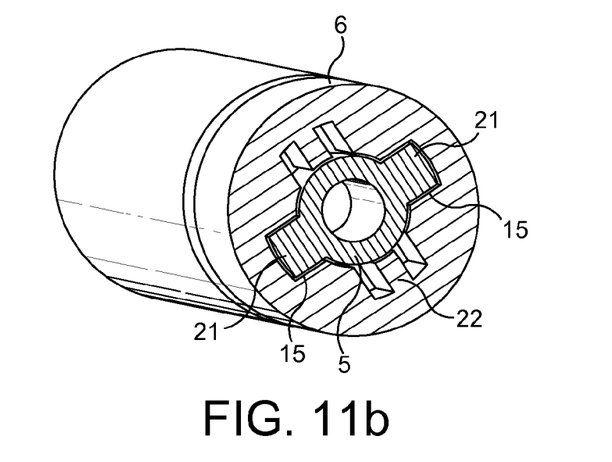
Figure 11C:
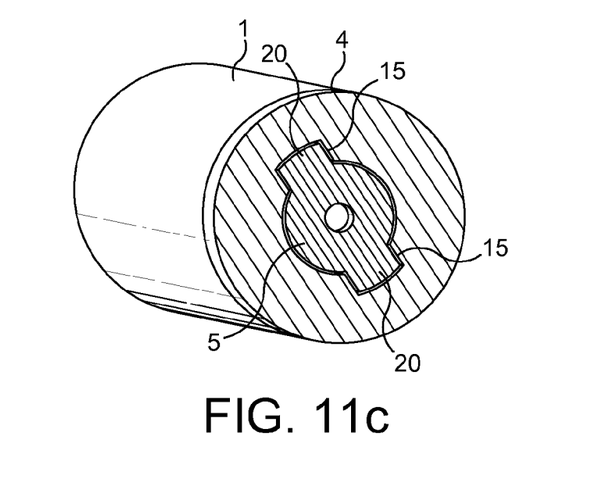

The nozzle member 5 also includes keys 21 that are received within axial slots 22 in the mouthpiece 6 as illustrated in FIGS. 9 and 10.

Figure 5:
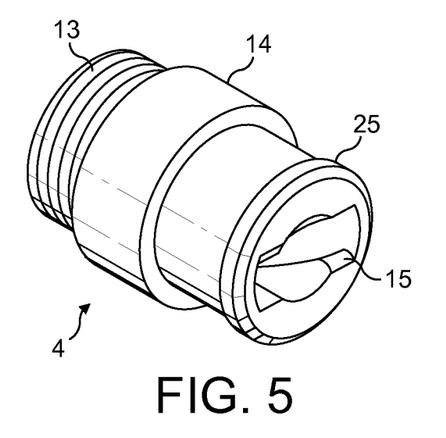
FIG. 5 is a perspective view of the body member shown in FIG. 4.
Figure 6:
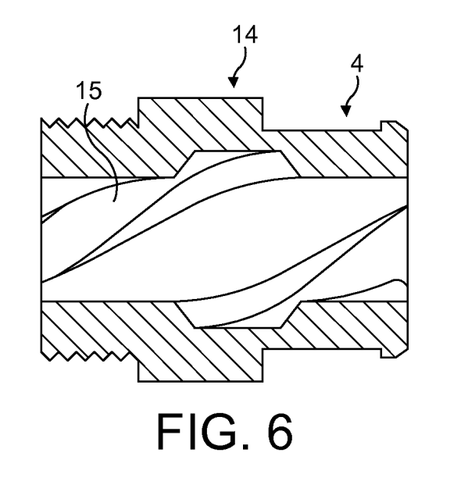
FIG. 6 is a longitudinal sectional view of the body member shown in FIG. 5.

As shown in FIG. 10, the mouthpiece 6 comprises a generally cylindrical body having a distal end with an enlarged bore region 23 with an interior, annular end channel 24 that can be push fitted onto annular ledge 25 on the body member 4 illustrated in FIG. 5. Once fitted, the mouthpiece 6 can rotate axially relative to the body member 4. Referring to FIG. 9, the mouthpiece 6 also includes axially extending ribs 26 which maintain the nozzle member 5 axially within the mouthpiece. A stop 27 limits axial movement of the keys 21 in the slots 22.

In use, when the mouthpiece 6 is rotated clockwise when viewed from the mouth end, the nozzle member 5 is rotated axially due to the engagement between the keys 21 on the nozzle member 5 and the slots 22 in the mouthpiece. The pegs 20 are guided by the thread 15 within the body member 4 so that upon rotation of the mouthpiece 6, the nozzle is guided by the thread 15 to be driven inwardly, towards the canister 2, and as a result, the discharge tube 9 is driven inwardly towards the valve 8 of the canister due to the stepped bore 17 shown in FIG. 8 being urged against the discharge tube 9.

As a result, the valve 8 is opened against the force of its interior spring 16 and a metered dose of fluid from within the canister 2 is ejected through the discharge tube that comprises the valve stem 9, into the nozzle member 5 to be formed into an aerosol as it passes through orifice 18 into the outlet tube 19. The outlet tube 19 leads into an enlarged outlet region 28 at the mouth or proximal end 29 of the device, for provision to a consumer. Thus, the consumer can dispense a metered dose of aerosol by twisting the body member 4 along with the canister housing 1 and canister 2 attached thereto, in a direction of arrow A relative to the mouthpiece 6, as illustrated in FIG. 1. The resulting aerosol spray 30 is illustrated in FIG. 4b.

It will be appreciated that after dispensation of the metered dose, the device is twisted in the direction of arrow B so that the process can be repeated. The rotation is limited by the keys 21 moving axially towards the mouth end 29 and abutting the stops 27. Also, spring 16 of the metered valve 8 assists in the return in the direction of arrow B.

The device may be actuated using two hands to grip the mouthpiece 6 and the canister housing 1 although it may be possible for the consumer to operate the device by holding the mouthpiece 6 between their lips and twisting the canister 1 in the direction of arrow A of FIG. 1.

Various modifications and variations fall within the scope of the invention. For example, visual clues may be provided on the canister to allow it to be oriented when installed so that the inlet tube 10 dips downwardly in normal use so all of the contents of the canister 2 can be readily consumed. Also, an interior spring may be provided to bias the mouthpiece 6 to normally assume the position shown in FIG. 4b, so that after a dose of aerosol has been dispensed, the device automatically assumes a configuration ready to dispense a further dose.

Furthermore, although the canister is described as an interchangeable element to allow the supply of liquid to be replenished, an integral pressurised supply vessel may be provided in the device, so that the device can be used multiple times and then discarded once the liquid supply has been exhausted from the vessel. In a modification, an inlet valve may be provided to allow the supply to be replenished from an exterior, pressurised source.

The valve 8 described herein is configured to deliver a metered dose on actuation but instead, a continuous flow valve could be used such that the consumer can maintain a flow of aerosol by continuously holding the device in the discharge position, allowing the consumer to control the aerosol dose.

The mouth end can be configured differently from that shown in the Figures. For example the mouth end could be a tapered cylindrical shape with flat piece for easy positioning and orientation cue in the mouth. Also, textured or rough finishes can be applied to the exterior surface of the mouthpiece to stimulate sensation in the lips.

In addition, soft plastic moulding may be provided on the canister housing or mouthpiece to act as grip points for the consumer to use when twisting the device to the discharge position. This moulding may also possess a textured surface to provide different touch sensations.

The supply tube of the pressurised canister may be of flexible construction and provided with a weighted end as to always assume the lowest position in the canister orientation and allow for complete consumption of the canister contents.

Inventive variations and aspects of the disclosure may include other non-limiting embodiments. For example, in one embodiment, an aerosol generator may comprise a body, a mouthpiece on the body, and a delivery mechanism operable to deliver aerosol for inhalation by a consumer into the mouthpiece by turning the mouthpiece and body relative to one another.

In one implementation, the body may include a mounting to receive a canister of pressurised liquid for forming the aerosol. In one implementation, the mounting may be configured to receive a canister including a discharge tube depressible inwardly to open a valve therein to release liquid from the canister through the discharge tube, and further including a nozzle member to be driven inwardly of the body upon said turning of the mouthpiece and body relative to one another, for depressing the discharge tube inwardly of the canister to open the valve.

In one implementation, the nozzle member may be in threading engagement with the body, the nozzle member having an end to abut the discharge tube of the canister, the nozzle member being coupled to the mouthpiece to rotate axially when the mouthpiece is rotated relative to the body and also to slide axially relative to the mouthpiece so as to be driven against the discharge tube of the canister to open the valve in the canister and discharge fluid into the nozzle member. In one implementation, the nozzle member may include a radially extending peg engaged in a helical groove in the body member to provide said threading engagement. In one implementation, the nozzle member is coupled to the mouthpiece by a key which engages with an axial groove in the mouthpiece to allow rotation of the nozzle member with the mouthpiece and axial sliding movement. In one implementation, the nozzle member includes an orifice to form an aerosol from the fluid discharged from the canister.

In one implementation, the generator may include a housing to receive the canister, the housing being releasably attached to the body member.

In one implementation, the body and the mouthpiece may be generally cylindrical with a common axis.

In one implementation, the generator may include the canister. In a further implementation. the canister may be generally cylindrical with a valve therein operable by an axially disposed discharge tube upon axial depression inwardly of the canister. In a further implementation, the canister may be arranged coaxially with the turning axis of the delivery mechanism.

The invention claimed is:

1. An aerosol generator comprising:
a housing configured to receive a canister,
a generally cylindrical body having a longitudinal axis and a mounting configured to receive the canister,
a mouthpiece mounted on the body for relative rotation about the longitudinal axis of the body, and
a delivery mechanism operable to deliver aerosol for inhalation by a consumer into the mouthpiece by turning the mouthpiece and body relative to one another about said axis, the delivery mechanism including a nozzle member to be driven inwardly of the body along said axis upon the turning of the mouthpiece and body relative to one another, for depressing the discharge tube inwardly of the canister to open the valve,
wherein the canister is disposed longitudinally fully within the housing, and
wherein the canister includes a discharge tube depressible inwardly to open a valve therein to release liquid from the canister through the discharge tube.

2. The generator according to claim 1, wherein the nozzle member is in threading engagement with the body, the nozzle member having an end to abut the discharge tube of the canister, the nozzle member being coupled to the mouthpiece to rotate axially when the mouthpiece is rotated relative to the body and to slide axially relative to the mouthpiece so as to be driven against the discharge tube of the canister to open the valve in the canister and discharge fluid into the nozzle member.

3. The generator according to claim 1, wherein the nozzle member includes a radially extending peg engaged in a helical groove in the body member to provide said threading engagement.

4. The generator according to claim 1, wherein the nozzle member is coupled to the mouthpiece by a key which engages with an axial groove in the mouthpiece allowing rotation of the nozzle member with the mouthpiece and axial sliding movement.

5. The generator according to claim 1, wherein the nozzle member includes an orifice configured to form an aerosol from the fluid discharged from the canister.

6. The generator according to claim 1, wherein the housing is releasably attached to the body member.

7. The generator according to claim 1, wherein the body and the mouthpiece are generally cylindrical with a common axis.

8. The generator according to claim 1, and including the canister engaged to the body.

9. The generator according to claim 8, wherein the canister is generally cylindrical with a valve therein operable by an axially disposed discharge tube upon axial depression inwardly of the canister.

10. The generator according to claim 8, wherein the canister is arranged coaxially with the longitudinal axis of the body.

11. An aerosol generator, comprising:
a housing configured to receive a canister,
a generally cylindrical body having a longitudinal axis and a canister mounting that engages a canister of pressurised aerosol forming liquid, wherein the mounting receives a canister including a discharge tube depressible inwardly to open a valve therein to release liquid from the canister through the discharge tube, with the canister disposed longitudinally fully within a housing; and
a mouthpiece mounted on the body for relative rotation about the longitudinal axis of the body, wherein the mouthpiece is configured to deliver the aerosol for inhalation by a consumer by axial rotation relative to the body,
wherein the canister is disposed longitudinally fully within the housing.

12. The aerosol generator of claim 11, wherein a nozzle member that is driven inwardly of the body upon said rotating depresses the discharge tube inwardly of the canister and opens the valve.

* * * * *